United States Patent [19]

Bayles et al.

[11] Patent Number: 5,155,236

[45] Date of Patent: Oct. 13, 1992

[54] PYRAN DERIVATIVES

[75] Inventors: Richard W. Bayles, Stockport; Anthony P. Flynn, Great Budworth; Ralph W. Turner, Cheadle, all of England

[73] Assignee: Imperial Chemical Industrial PLC, London, England

[21] Appl. No.: 334,749

[22] Filed: Apr. 6, 1989

Related U.S. Application Data

[63] Continuation of Ser. No. 942,437, Dec. 16, 1986, abandoned.

[30] Foreign Application Priority Data

Dec. 23, 1985 [GB] United Kingdom ............... 8531638

[51] Int. Cl.$^5$ ................................. C07D 309/06
[52] U.S. Cl. ........................................ 549/291
[58] Field of Search ............................ 549/291

[56] References Cited

U.S. PATENT DOCUMENTS

| | | | |
|---|---|---|---|
| 3,248,187 | 4/1966 | Bell, Jr. .................. | 549/291 |
| 4,269,772 | 5/1981 | Melillo et al. ............ | 260/245 |
| 4,282,148 | 8/1981 | Liu et al. ................ | 260/239 |
| 4,287,123 | 9/1981 | Liu et al. ................ | 260/239 |
| 4,312,871 | 1/1982 | Christensen et al. ...... | 540/351 |
| 4,341,791 | 7/1982 | Christensen et al. ...... | 540/351 |
| 4,344,885 | 7/1982 | Liu et al. ................ | 549/291 |
| 4,349,687 | 9/1982 | Liu et al. ................ | 549/291 |
| 4,491,659 | 1/1985 | Durette .................. | 549/291 |
| 4,559,406 | 12/1985 | Lempert et al. ........... | 549/291 |
| 4,837,343 | 6/1989 | Hatanaka ................. | 549/291 |

FOREIGN PATENT DOCUMENTS

0260092 9/1987 European Pat. Off. .
2569194 8/1986 France .

OTHER PUBLICATIONS

Shih et al Heterocycles, vol. 21, pp. 29-40 (1984).
Shih et al Tetrahedron Letters vol. 26, pp. 583-586.
Hatanaka et al Chemical Absts. 108:21560W.
McElvain et al; Ketene Acetals. XXXII. "The Condensation of Ketene Dimethylacetal with Various Aldehydes and Ketones" pp. 5736-5739, JACS, vol. 76 (1954).
Bakker et al; Journal of the Royal Netherlands Chemical Society, 100, Jan. 1, 1981; ZnCl$_2$–catalysed cycloadditions between ketene acetals and x$\beta$-unsaturated carbonyl compounds. A simple route to 2,2–dialkoxy-3,-4–dyhydropyrans.
Aben et al; Tetrahedron Letters, vol. 26, No. 15 pp. 1889–1892, 1985; High pressure–promoted cycloadditions of ketene acetals and x$\beta$-unsaturated aldehydes and ketones.
Thuy, Vu Moc; Bull. Chim. Soc. (France). 1970 p. 4429; Action des organomagnesiens sur les diacoxy-2,2 dihydro-3,4 2H-pyrannes.
Minoru Hatanaka; Tetrahedron Letters, vol. 28, No. 1, pp. 33–36, 1987; A Stereoselective approach to 18-Methylcarbapenem Antibiotic starting . . . Ester.
Nagahara et al; Heterocycles vol. 25, 729 (1987).
S. Hanessian et al, Can. J. Chem., vol. 60 (1982), pp. 2292–2294.
Chemical Abstract No. 100:156938f (abstract of JP 58–174,377) (1983).

*Primary Examiner*—Richard L. Raymond
*Assistant Examiner*—Mark W. Russell
*Attorney, Agent, or Firm*—Cushman, Darby & Cushman

[57] ABSTRACT

Compounds of formula I:

(I)

wherein:
R1 is hydrogen or alkyl;
R2 is alkyl optionally substituted by one or more alkoxy groups or halogen atoms;
X is a group of formula —OR3 wherein R3 is alkyl, cycloalkyl, or arylalkyl; or X is a group of formula —NHCVR4 wherein V is oxygen or sulphur, R4 is hydrogen, alkyl, cycloalkyl (which alkyl and cycloalkyl groups may be substituted), alkenyl, aryl, arylalkyl, amino, mono- or di-alkylamino or a group of the formula —OR5 wherein R5 is optionally substituted alkyl, aryl or arylalkyl; or X is a group of formula —NHSO$_2$R4a wherein R4a is alkyl, aryl or a group of formula —CH$_2$COR4b wherein R4b is alkyl or aryl;
Y is optionally substituted alkoxy, cycloalkoxy, arylalkoxy or a group of formula —NR6R7 wherein R6 is hydrogen or alkyl and R7 is alkyl, cycloalkyl (which alkyl and cycloalkyl groups may be substituted), aryl or arylalkyl or R7 is a group of formula —COOR8 wherein R8 is alkyl are useful intermediates in the synthesis of beta-lactam antibiotics.

9 Claims, No Drawings

PYRAN DERIVATIVES

This is a continuation division of application Ser. No. 06/942,437, filed Dec. 16, 1986 now abandoned.

The invention relates to compounds useful as intermediates in the synthesis of beta-lactam antibiotics, particularly carbapenems, and to a process for the manufacture of the said compounds.

In this specification chemical formulae (denoted by Roman numerals) are set out graphically on separate sheets. Numbered groups, e.g. R1, R2 etc. used in more than one formula are to be taken as having the same meaning throughout the specification unless otherwise stated.

Unless otherwise indicated herein alkyl means (1-6 C)alkyl, cycloalkyl means (3-7 C)cycloalkyl or bridged (6-9 C)bicycloalkyl, aryl means an optionally substituted 5- or 6-membered carbocyclic or heterocyclic aryl group (containing, when heterocyclic, 1, 2 or 3 heteroatoms selected from O, N and S), arylalkyl means aryl(1-4 C)alkyl, alkoxy means (1-6 C)alkoxy, cycloalkoxy means (3-7 C)cycloalkoxy or bridged (6-9 C)bicycloalkoxy and alkenyl means (2-6 C)alkenyl.

In first aspect the invention provides compounds of formula I wherein:

R1 is hydrogen or alkyl;
R2 is alkyl optionally substituted by one or more alkoxy groups or halogen atoms;
X is a group of formula —OR3 wherein R3 is alkyl, cycloalkyl, or arylalkyl; or X is a group of formula —NHCVR4 wherein V is oxygen or sulphur, R4 is hydrogen, alkyl, cycloalkyl (which alkyl and cycloalkyl groups may be substituted), alkenyl, aryl, arylalkyl, amino, mono- or di-alkylamino or a group of the formula —OR5 wherein R5 is optionally substituted alkyl, aryl or arylalkyl; or X is a group of formula —NH-SO$_2$R4a wherein R4a is alkyl, aryl or a group of formula —CH$_2$COR4b wherein R4b is alkyl or aryl; Y is optionally substituted alkoxy, cycloalkoxy, arylalkoxy or a group of formula —NR6R7 wherein R6 is hydrogen or alkyl and R7 is alkyl, cycloalkyl (which alkyl and cycloalkyl groups may be substituted), aryl, arylalkyl or R7 is a group of formula —COOR8 wherein R8 is alkyl or arylalkyl;

In a particular aspect the invention provides compounds of formula I wherein:

R1 is hydrogen or (1-4 C)alkyl;
R2 is alkyl optionally substituted by one or more (1-4 C)alkoxy groups or halogen atoms;
X is a group of formula —OR3 wherein R3 is alkyl, cycloalkyl, or arylalkyl; or X is a group of formula —NHCVR4 wherein V is oxygen, R4 is hydrogen, alkyl, cycloalkyl (which alkyl and cycloalkyl groups may be substituted), alkenyl, aryl, arylalkyl, amino, mono-or di-(1-4 C)alkylamino or a group of the formula —OR5 wherein R5 is optionally substituted alkyl, aryl or arylalkyl; or X is a group of formula —NHSO$_2$R4a wherein R4a is alkyl, aryl or a group of formula —CH$_2$COR4b wherein R4b is alkyl or aryl;

Y is optionally substituted alkoxy, cycloalkoxy, arylalkoxy or a group of formula —NR6R7 wherein R6 is hydrogen or (1-4 C)alkyl and R7 is (1-4 C)alkyl, cycloalkyl (which alkyl and cycloalkyl groups may be substituted), aryl, arylalkyl, or R7 is a group of formula —COOR8 wherein R8 is (1-4 C)alkyl or arylakyl;

Where any of the above alkyl or cycloalkyl groups are substituted, the substituent(s) may be for example one or more halogen (e.g. fluorine or chlorine) atoms or alkoxy groups unless otherwise specified.

Optional substituent(s) on an alkyl group R5 may be for example one or more halogen (e.g. fluorine or chlorine) atoms.

An optional substituent on an alkoxy or cycloalkoxy group Y may be for example a carboxy or (1-4 C)alkoxycarbonyl group.

Optional substituent(s) on an aryl group herein may be for example halogen, alkyl, (1-4 C)alkoxy or (2-6 C)alkoxycarbonyl.

Particular meanings for R1 are hydrogen or a methyl group.

A particular meaning for R2 is methyl, optionally substituted by one or more fluorine atoms.

Particular meanings for the group X are methoxy, ethoxy or benzyloxy or a group of the formula —NHCOR$_4$ wherein R4 is hydrogen or methyl, ethyl, ethenyl, phenyl, benzyl, methoxy, ethoxy, amino, trifluoroethoxy, trichloroethoxy, phenoxy or benzyloxy.

Particular meanings for the group Y are methoxy, ethoxy or benzyloxy or a group of the formula NR6R7 wherein R6 is hydrogen and R7 is methyl, ethyl, phenyl, benzyl, α-methylbenzyl, methoxycarbonyl or ethoxycarbonyl.

A particular meaning for an aryl group is phenyl and particular meanings for the optional substituent(s) on the phenyl group are fluorine, chlorine, bromine, methyl, ethyl, methoxy, ethoxy, methoxycarbonyl or ethoxycarbonyl.

The compounds of formula I may be prepared from compounds of formula II wherein R9 is (1-12 C)alkyl, cycloalkyl (which alkyl and cycloalkyl groups may be substituted) or arylalkyl, by reduction e.g. with sodium borohydride or a hydrosilane or trialkylsilane (e.g. triethylsilane) in acid solution (e.g. in trifluoroacetic acid), conveniently at room temperature.

The compounds of formula II are novel and form a further feature of the invention.

Optional substituents on an alkyl or cycloalkyl group R9 may be for example one or more halogen (e.g. fluorine or chlorine) atoms, hydroxy or alkoxy groups.

Particular meanings for R9 are methyl, ethyl, benzyl.

The compounds of formula II may in turn be prepared by one of the following methods:

METHOD (1)

Hydrolysis of a compound of formula III wherein R10 and R11 (which may be the same or different) are selected from (1-12 C)alkyl, cycloalkyl (which alkyl and cycloalkyl groups may be substituted) arylalkyl or silyl (bearing alkyl, aryl or arylalkyl substituents) or R10 and R11 are joined to form a 5- or 6-membered cyclic acetal which may be substituted, e.g. by alkyl, carboxy or (1-7 C)alkoxycarbonyl. The hydrolysis is conveniently carried out under acid condition e.g. with dilute mineral acid e.g. HCl preferably in an organic solvent e.g. methanol, ethanol, tetrahydrofuran, conveniently at room temperature.

Particular meanings for R10 and R11 are methyl, ethyl, benzyl, trimethylsilyl and dimethyl-t-butylsilyl.

The compounds of formula III may themselves be prepared by reaction of a compound of formula IV with a compound of formula V.

The compounds of formula (IV), and the compounds of formula (V) wherein R10 and R11 are not the same, can each exist in two isomeric forms and the process of the invention extends to the use of either of each pair of isomers separately or of mixtures of isomers.

The reaction between the compounds of formulae IV and V is conveniently carried out in an organic solvent e.g. toluene, xylene, acetonitrile, a halogenated hydrocarbon (e.g. methylene chloride, chloroform), or an ether (e.g. diethyl ether, tetrahydrofuran, dioxan) optionally in the presence of a catalyst, e.g. a Lewis acid catalyst, for example a rare earth complex. The use of the catalyst may influence the overall yield of the product and also the relative amounts of the isomers of products of formula (III) about the C3 and C4 positions which are produced. The reaction is conveniently carried out at temperatures up to about 120° C. for example from 0°-100° C.

METHOD (2)

Reaction of a compound of formula IV with a compound of formula V directly, in particular where one or both of R10 and R11 represents a silyl group and the reaction is carried out as described above but in the presence of a titanium tetrachloride or fluoride ion catalyst.

The compounds of formula I are, as stated, useful intermediates in the preparation of beta-lactam antibiotics. Thus they may be converted, by simultaneous or sequential hydrolysis of the groups X and Y (e.g. by heating with strong acid, e.g. HCl) to compounds of the formula VI. The compounds of formula VI wherein R1 is other than hydrogen are themselves novel and form further features of the invention.

Compounds of formula VI may be converted, by methods known in the literature for analogous compounds or by methods analogous to such methods, (for example D G Melillo, I Shinkai, T Liu, K Ryan and M Sletzinger, Tetrahedron Letters, vol. 21, p. 2783 (1980)) to azetidinones of the formula VII, where R12 is for example an alkyl or aralkyl group, e.g. a methyl or benzyl group.

Compounds of formula VII are known to be useful intermediates for the production of antibiotics, in particular carbapenem antibiotics.

It will be understood that compounds of formula VII contain up to four asymmetric centres. It is desirable that the said compounds should have the sterochemistry illustrated in formula VIIa and the process of the invention is advantageously operated in such a way that compounds having the formula VIIa may be produced e.g. by chiral synthesis, if necessary after subsequent treatment and/or separation of isomers or by resolution of optical isomers at a suitable stage. Achievement of the correct stereochemistry in the compound of formula VIIa may be facilitated by the use of compounds in which one or more of the groups R9, R10, X and Y are chiral.

The invention is illustrated, but not limited, by the following Examples, in which n.m.r. means nuclear magnetic resonance spectroscopy, m.p. means melting point and b.p,. means boiling point. The n.m.r. spectra were taken at 200 MHz in the solvent indicated and are quoted in delta values in parts per million (ppm). In the quotation of the n.m.r. spectra standard abbreviations are used e.g. s=singlet, d=doublet, q=quartet, m=multiplet, br=broad.

EXAMPLES 1-25

Compounds of formula III may be prepared as follows:

EXAMPLE 1

N-Ethoxycarbonyl-2-ethoxymethylene-3-oxobutanamide (2.3 g) was dissolved in toluene (15 ml) and treated dropwise with 1,1-di-ethoxyprop-1-ene (2 g). The mixture was stirred at 40° C. for 2 hours and evaporated to dryness. The residual oil was purified by medium pressure liquid chromatography on K60 silica using ethyl acetate/petroleum ether b.p. 60°-80° C. 15/85 v/v and 20/80 v/v as eluting solvents, to give after trituration with n-hexane trans-2,2-diethoxy-3,6-dimethyl-4-ethoxy-N-ethoxycarbonyl-3,4-dihydro-2H-pyran5-carboxamide (0.6 g) m.p. 84°-7° C. The n.m.r. spectrum in deuterochloroform displayed the —CH(OEt)— signal at 3.9 ppm (doublet of quartets, 1H J=3 Hz and 1 Hz), which is indicative of the trans arrangement of the 3 and 4 substituents.

EXAMPLE 2

N-ethoxycarbonyl-2-ethoxymethylene-3-oxobutanamide (1.2 g) and tris(6,6,7,7,8,8,8-heptafluoro-2,2-dimethyl-3,5-octanedionato)ytterbium (0.27 g) were stirred in toluene (10 ml) and 1,1-diethoxyprop-1-ene (1 g) was added dropwise. The mixture was stirred at room temperature for three hours and evaporated to dryness. The residual oil was partitioned between diethyl ether and water and the organic layer was separated, dried over anhydrous magnesium sulphate, and evaporated to dryness. The residual oil was purified by medium pressure liquid chromatography on K60 silica using ethyl acetate/petroleum ether, b.p. 60°-80° C., 15/85 v/v and 20/80 v/v as eluting solvents to give, after trituration with n-hexane, trans-2,2-diethoxy-3,6-dimethyl-4-ethoxy-N-ethoxycarbonyl-3,4-dihydro-2H-pyran-5-carboxamide (0.5 g), m.p. 86°-8° C.

EXAMPLE 3

N-(4'-Chlorophenyl)-2-ethoxymethylene-3-oxobutanamide (1.3 g) was stirred in toluene (10 ml) whilst 1,1-diethoxyprop-1-ene (2 g) was added dropwise. The mixture was stirred at room temperature for 40 hours and evaporated to dryness. The residual gum was purified by medium pressure liquid chromatography on K60 silica using ethyl acetate/petroleum ether b.p. 60°-80° C. 15/85 v/v as eluting solvent to give two stereoisomers. The first isomer after trituration with n-hexane gave trans-N-(4'-chlorophenyl)-2,2-diethoxy-3,6-dimethyl-4-ethoxy-3,4-dihydro-2H-pyran-5-carboxamide (0.6 g), m.p. 104°-106° C. The n.m.r. spectrum (deuterochloroform) showed the —CH(OEt)— signal at 4.0 ppm (doublet of quartets 1H, J=3 Hz and 1 Hz), consistent with the transconfiguration. The second isomer, after trituration with n-hexane, gave cis-N-(4'-chlorophenyl)-2,2-diethoxy-3,6-dimethyl-4-ethoxy-3,4-dihydro-2H-pyran-5-carboxamide (0.1 g), m.p. 125°-7° C. The n.m.r. spectrum (deuterochloroform) showed the —CH(OEt)—signal at 4.5 ppm (doublet of quartets, 1H, J=7 Hz and 1 Hz) consistent with the cis-configuration.

EXAMPLE 4

N-(4'-Chlorophenyl)-2-ethoxymethylene-3-oxobutanamide (1.3 g) and tris (6,6,7,7,8,8,8-heptafluoro-2,2-dimethyl-3,5-octanedianato)ytterbium (0.26 g) were stirred in toluene (10 ml) whilst 1,1-diethoxyprop-1-ene (2 g) was added dropwise. The mixture was stirred at room temperature for two hours and evaporated to dryness. The residual gum was purified by medium pressure liquid chromatography on K60 silica using ethyl acetate/petroleum ether b.p. 60°-80° C., 15/85 v/v as eluting solvent to give two stereoisomers. The first isomer after trituration with n-hexane gave trans-N-(4'-chlorophenyl)-2,2-diethoxy-3,6-dimethyl-4-ethoxy-3,4-dihydro-2H-pyran-5-carboxamide (0.2 ), m.p. 104°-106° C. The second isomer, again after trituration with n-hexane, gave cis-N-(4'-chlorophenyl)-2,2-diethoxy-3,6-dimethyl-4-ethoxy-3,4-dihydro-2H-pyran-5-carboxamide (1.3 g), m.p. 125°-127° C.

EXAMPLE 5

N-(4'-chlorobenzyl)-2-ethoxymethylene-3-oxobutanamide (1.4 g) and tris (6,6,7,7,8,8,8-heptafluoro-2,2-dimethyl-3,5-octanedianato)ytterbium (0.26 g) were stirred in toluene (10 ml) whilst 1,1-diethoxyprop-1-ene (4 g) was added dropwise. The mixture was stirred at room temperature for 3 days and evaporated to dryness. The residual gum was triturated with petroleum ether b.p. 60°-80° C. to give a solid which was recrystallised from a mixture of toluene and petroleum ether b.p. 60°-80° C. to give cis-N-(4'-chlorobenzyl)-2,2-diethoxy-3,6-dimethyl-4-ethoxy-3,4-dihydro-2H-pyran-5-carboxamide (0.9 g) m.p. 97°-100° C.

The n.m.r. spectrum in deuterochloroform displayed the —CH(OEt)— signal at 4.5 ppm (doublet of quartets, 1H, J=7 Hz).

EXAMPLE 6

1,1-Diethoxyprop-1-ene (5.0 ml) was added in one portion to a stirred solution of methyl-2-acetylaminomethylene-3-oxobutanoate (5.2 g) in toluene (15 ml) at 20°-25° C. An exothermic reaction ensued and a crystalline solid precipitated out. The reaction mixture was stirred for 2 further hours at ambient temperature and the solid was then filtered off to give methyl trans-4-acetylamino-2,2-diethoxy-3,6-dimethyl-3,4-dihydro-2H-pyran-5-carboxylate (4.0 g), m.p. 152°-154° C. The structure of this ester was ascertained using X-ray analysis. The n.m.r. spectrum in deuterochloroform showed a signal for the —CH(N)— proton at 4.85 ppm (doublet of doublets of quartets, $J_{3,4}=1.5$, $J_{4,NH}=9.8$, $J_{4,7}=0.9$ Hz, $C_6Me=C_7$).

The filtrate was evaporated to dryness and the residual gum dissolved in boiling hexane. After charcoal treatment the residual solution on cooling gave crystalline methyl cis-4-acetylamino-2,2-diethoxy-3,6-dimethyl-3,4-dihydro-2H-pyran-5-carboxylate (3.0 g), m.p. 87°-88° C. The n.m.r. spectrum in deuterochloroform displayed the —CH(N)— proton at 5.12 ppm. (doublet of doublets of quartets $J_{3,4}=5.4$, $J_{4,NH}=10.2$, $J_{4,7}=0.9$ Hz).

EXAMPLES 7–16

The procedure of Example 6 was used to prepare the compounds of Examples 7-16, details of which are given in Table I, except that chromatography on K60 silica, eluting with diethyl ether-hexane mixture, was used to separate cis and trans isomers before crystallisation.

TABLE I

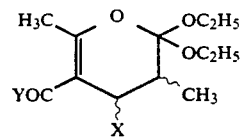

| Example No. | Y | X | trans:cis ratio | Mpt °C. trans | Mpt °C. cis |
|---|---|---|---|---|---|
| 7 | OCH$_3$ | NHCOPh | 1.1:1 | 105–7 | 124–5 |
| 8 | OCH$_3$ | NHCHO | 1.5:1 | 113–5 | (N/I) |
| 9 | OCH$_3$ | NHCOOCH$_2$Ph | 1:1 | N/I | 72–4 |
| 10 | OCH$_3$ | NHCOCH$_2$Cl | 1.3:1 | 122–4 | (N/I) |
| 11 | OCH$_3$ | NHCOC(CH$_3$)$_3$ | 1:2 | (N/I) | 81–2 |
| 12 | OCH$_3$ | NHCOOCH$_2$CCl$_3$ | 1:1 | (N/I) | 97–9 |
| 13 | OCH$_2$CH$_3$ | NHCONH$_2$ | 3.5:1 | 148–9 | (N/I) |
| 14 | OCH$_3$ | NHCOCH=CH$_2$ | 1.8:1 | 134–6 | (N/I) |
| 15 | OCH$_3$ | NHCOCCl$_3$ | 1.3:1 | oil[1] | oil[1] |
| 16 | OCH$_2$Ph | NHCOOCH$_2$Ph | 1:1 | 70–2 | oil[2] |

(Ph = Phenyl) (N/I = not isolated)

Footnotes
[1] n.m.r. (CDCl$_3$) trans: 1.00(d, 3H), 1.20(t, 3H), 1.30(t, 3H)2.36(d, 3H), 2.37(dq, 1H), 3.59(q, 2H), 3.70(m, 2H), 3.72(s, 3H), 4.80(ddq, 1H). The cis-isomer was characterised by n.m.r. signals at 1.10(d, 3H) and 5.03(ddq).
[2] n.m.r. (CDCl$_3$): 1.07(d, 3H), 1.15(t, 3H), 1.23(t, 3H), 2.25(s, 3H), 2.27(dg, 1H), 3.60(m, 2H), 3.80(m, 2H), 4.90(ddq, 1H), 5.04(s, 2H), 5.13(s, 3H), 5.28(d, 1H), 7.30(m, 10H).

EXAMPLE 17

1,1-Diethoxyprop-1-ene (1.0 ml) was added to a solution of methyl 2-acetylaminomethylene-3-oxobutanoate (1.0 g) and tris (6,6,7,7,8,8,8-heptafluoro-2,2-dimethyl-3,5-octandionato)ytterbium (0.05 g) in toluene (3.0 ml) at 20° C. After stirring for 2 hr at ambient temperature, the reaction mixture was filtered to give methyl trans-4-acetylamino-2,2diethoxy-3,6-dimethyl-3,4-dihydro-2H-pyran-5-carboxylate (1.05 g), m.p. 153°–4° C.

EXAMPLE 18

N-(4'-chlorophenyl)-2-(acetylaminomethylene)-3-oxobutanamide (83 g) in toluene (200 ml) was treated with 1,1-diethoxyprop-1-ene (60 ml) and heated at 100° C. for 6 hours. The mixture was evaporated and the residue was triturated with toluene to give trans-2,2-diethoxy-3,6-dimethyl-4-(acetylamino)-5-(4'-chlorophenylcarbamoyl)-3,4-dihydro-2H-pyran (80.5 g) m.p. 199°–201° C.

The general process of Example 18 was repeated using the appropriate diene compound to yield the compounds of Examples 19–22, of which details are given in Table II, all of the compounds being trans about the 3,4 bond.

TABLE II

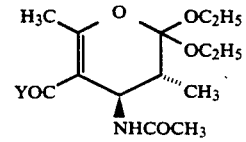

| Example No. | Y | Melting point (°C.) | |
|---|---|---|---|
| 19 | C$_2$H$_5$OCONH— | 75–80 | |
| 20 | PhCH(CH$_3$)CONH—(S) | 210–2 | (3R,4R)[1] |
| 21 | PhCH(CH$_3$)CONH—(S) | 157–8 | (3S,4S)[1] |

TABLE II-continued

![structure: H3C-C(=O)... YOC... with OC2H5, OC2H5, CH3, NHCOCH3]

| Example No. | Y | Melting point (°C.) | |
|---|---|---|---|
| 22 | PhCH(CH3)CONH—(R) | 158-60 | (3R,4R) |

Footnote
[1]The products were purified by chromatography on K60 silica using diethyl ether as eluting solvent and subsequent recrystallisation from a mixture of diethyl ether and hexane. The structure of the two diastereoisomers were determined by X-ray analysis.

EXAMPLE 23

To a stirred solution of methyl 2-acetylamino methylene-3-oxobutanoate (18.5 g) in toluene (100 ml) at 20°-25° C. was added 1,1-dimethoxy ehtene (15 ml) in one portion. An exothermic reaction ensued and a crystalline solid formed, which was filtered off after stirring for 2 hours at ambient temperature to give methyl 4-acetylamino-2,2-dimethoxy-6-methyl-3,4-dihydro-2H-pyran-5-carboxylate (26.2 g) m.p. 160°-2° C., n.m.r. (CDCl3) 1.95 (s,3H), 1.98 (dd,1H), 2.27 (dd,1H), 2.27 (dd,1H), 2.30 (d,3H), 3.32 (s,3H), 3.40 (s, 3H), 3.72 (s,3H), 5.21 (ddq, 1H), 5.95 (d,1H).

PREPARATION OF STARTING MATERIALS FOR EXAMPLES 1-23

Compounds of formula IV used as starting materials in the preparation of compounds of formula III may be prepared for example by the following methods. Where no specific method of preparation for such a starting material is given, the compound is known in the literature and/or may be prepared by methods analogous to those given.

The ketene acetals of formula V (e.g. 1,1-diethoxy-prop-1-ene) may be prepared for example by the method of J Amer Chem Soc. 62, 1482 (1940) or German Patent Application DE 2331675.

PREPARATION 1

N-(4'-chlorobenzyl)-2-ethoxymethylene-3-oxobutanamide (starting material for Example 5)

N-4'-chlorobenzyl-3-oxobutanamide (13 g), triethoxymethane (16 ml) and acetic anhydride (25 ml) were refluxed for 1.5 hours. The reaction mixture was evaporated, the residual gum was triturated with ether and the resulting solid was recrystallised from a mixture of ethyl acetate and petroleum ether b.p. 60°-80° C. to give the title compound (7.5 g) m.p. 103°-5° C.

PREPARATION 2

Methyl 2-acetylaminomethylene-3-oxobutanoate (starting material for Examples 6 and 23)

Acetamide (10.0 g) and methyl 2-methoxymethylene-3-oxobutanoate (30.0 ml) were heated with stirring at 100° C. for 4 hours. On cooling the product was flash chromatographed on Merck silica 9385 using a 50/50 mixture of ether/hexane to give the title compound (18.5 g) m.p. 60°-62° C. (hexane/ether).

PREPARATION 3

Methyl 2-trichloroacetamidomethylene-3-oxobutanoate (starting material for Example 15)

Methyl 2-aminomethylene-3-oxobutanoate (1.4 g) in methylene chloride (20 ml) was treated with triethylamine (2.0 ml) and trichloroacetyl chloride (2.0 ml) while stirring at 20°-25° C. The mixture was stirred for 4 hours at 20° C. to give a solution of the title compound, which was used immediately to prepare the dihydropyran of Example 15 without isolation.

PREPARATION 4

N-(4'-chlorophenyl)-2-(N-acetylaminomethylene-3-oxobutanamide (starting material for Example 18)

N-(4'-chlorophenyl)-2-ethoxymethylene-3-oxobutanamide (108 g), acetamide (31 g) and toluene (20 ml) were heated at 140° C. for 5 hours. The mixture was evaporated and the residue was triturated with diethyl ether to give the title compound (83.2 g) m.p. 132°-6° C.

PREPARATION 5

Benzyl 2-benzylcarbonylaminomethylene-3-oxobutanoate (starting material for Example 16)

A mixture of benzyl acetoacetate (20 ml), tribenzyl orthoformate (38 ml), benzyl carbamate (15 g) and acetic anhydride (40 ml) was stirred at reflux temperature (130°-140° C.) for 16 hours. The solvents were evaporated at reduced pressure and the residue purified by chromatography on K60 silica eluting with Et2O/hexane (1:5) to give the title compound as an oil. n.m.r. (CDCl3): 2.50 (s,3H), 5.20 (s,4H), 7.37 (m,10H), 8.47 (d, 1H).

PREPARATION 6

(a) N-[(S)-1'-phenylethyl]-2-acetylaminomethylene-3-oxobutanamide (starting material for Examples 20 and 21) was prepared by the method of Preparation 4 and purified by chromatography on K60 silica using toluene as eluant, n.m.r. (CDCl3): 1.5 (d,3H), 2.2 (s,3H), 2.4 (s,3H), 5.1 (m,1H), 7.3 (m,5H), 8.5 (d,1H).

(b) N-[(R)-1'-phenylethyl]-2-acetylaminomethylene-3-oxobutanamide (starting material for Example 22) was prepared by the method of Preparation 4 and purified by chromatography on K60 silica using diethyl ether-hexane (70-30, v/v) as eluant and recrystallisation from hexane.

PREPARATIONS 7-14 (Starting materials for the corresponding Examples 7-14)

The compounds indicated in Table III were prepared by the methods specified.

TABLE III

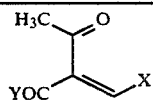

| Preparation No. | Y | X | M.pt. (°C.) | Prepared according to process of Preparation No: |
|---|---|---|---|---|
| 7 | OCH3 | NHCOPh | 89-90 | 5 |
| 8 | OCH3 | NHCHO | 90-91 | 2 |
| 9 | OCH3 | NHCO2CH2Ph | 95-7 | 2 |

TABLE III-continued $$\underset{YOC}{\overset{H_3C}{\diagdown}}\underset{}{\overset{O}{\diagup}}\underset{X}{\diagdown}$$

| Preparation No. | Y | X | M.pt. (°C.) | Prepared according to process of Preparation No: |
|---|---|---|---|---|
| 10 | OCH$_3$ | NHCOCH$_2$Cl | 78–80 | 2 |
| 11 | OCH$_3$ | NHCOC(CH$_3$)$_3$ | oil[1] | 2 |
| 12 | OCH$_3$ | NHCO$_2$CH$_2$CCl$_3$ | Note[2] | 3 |
| 13 | OCH$_2$CH$_3$ | NHCONH$_2$ | 194–6 | 5 |
| 14 | OCH$_3$ | NHCOCH=CH$_2$ | 74–6 | 2 |

Footnotes
[1]The product was purified by chromatography on K60 silica using ether/hexane (1:4) as eluant, n.m.r. (CDCl$_3$): 1.3(s, 9H), 2.5(s, 3H), 3.8(s, 3H), 8.6(d, 1H), 12.4(broad, 1H)
[2]The solution in methylene chloride was used immediately to prepare the dihydropyran.

PREPARATION 15

N-Ethoxycarbonyl-2-acetylaminomethylene-3-oxobutanamide (starting material for Example 19) was prepared according to the method of Preparation 4, m.p. 110°–3° C.

EXAMPLES 24–26

The following Examples illustrate the preparation of compounds of formula II. Analogous methods may be employed using the remaining compounds of formulae III prepared in Examples 1–23 as starting materials, to obtain further compounds of formula II.

EXAMPLE 24

To a solution of methyl trans-4-acetylamino-2,2-diethoxy-3,6-dimethyl-3,4-dihydro-2H-pyran-5-carboxylate (12.2 g) (Example 6) in 200 ml tetrahydrofuran was added 3.0 ml water and 1.0 ml 1N HCl. The mixture was stirred at 20°–25° C. for 16 hours, then neutralised by adding 1.0 g anhydrous potassium carbonate. The mixture was filtered and the filtrate evaporated at reduced pressure to give 11.4 g of crude product which was crystallised from toluene/hexane (50:50) giving ethyl 2-methyl-3-acetylamino-4-methoxycarbonyl-5-oxohexanoate (6.8 g), m.p. 93°–6° C.

EXAMPLE 25

Trans-2,2-diethoxy-3,6-dimethyl-4-acetylamino-5-(4'-chlorophenylcarbamoyl)-3,4-dihydro-2H-pyran (76.5 g) (Example 18) was stirred at room temperature in a mixture of tetrahydrofuran (200 ml) and 1N hydrochloric acid (10 ml) for 16 hours. The reaction mixture was diluted with water, extracted with ethyl acetate and the organic extract dried in anhydrous magnesium sulphate and evaporated to dryness. The residual solid was triturated with diethyl ether to give ethyl 2-methyl-3-acetylamino-4-(4'-chlorophenylcarbamoyl)-5-oxohexanoate, 66 g, m.p. 169°–73° C.

EXAMPLE 26

The above method was used to prepare ethyl-2-methyl-3-acetylamino-4-[(S)-1'-phenylethylcarbamoyl]-5-oxohexanoate, m.p. 189°–90° C. from the compound of Example 21.

EXAMPLES 27–31

The following Examples illustrate the preparation of the compounds of formula I, either from compounds of formula II as isolated in Examples 24–26, or from compounds of formula III as prepared in Examples 1–23 without isolation of the intermediate compound of formula II. Analogous methods can be used to prepare further compounds of formula I from the remaining compounds of formula III described in Examples 1–23.

EXAMPLE 27

To a solution of ethyl 2-methyl-3-acetylamino-4-methoxycarbonyl-5-oxohexanoate (2.9 g) (Example 24) in trifluoracetic acid (25 ml) at 20°–25° C. was added triethylsilane (4 ml). The mixture was stirred for 48 hrs., then the solvent was evaporated at reduced pressure.

By chromatography on K60 silica with ethyl acetate as eluant, three isomers of 2-oxo-3,6-dimethyl-4-acetylamino-5-methoxycarbonyl-3,4,5,6-tetrahydro-2H-pyran were separated:

the 3,4-trans, 4,5-trans, 5,6-trans (ttt) isomer, 1 g., m.p. 155°–6° C. n.m.r. (CDCl$_3$): 1.38 (d,3H), 1.39 (d,3H), 1.98 (s,3H), 2.64 (dq,1H), 2.79 (dd,1H), 3.73 (s,3H),, 4.26 (ddd,1H), 4.58 (d,1H), 6.0 (d,1H)

the 3,4-trans, 4,5-trans, 5,6-cis(ttc)isomer, 0.3 g., m.p. 109°–110° C., n.m.r. (CDCl$_3$): 1.30 (d,3H), 1.39 (d,3H), 2.01 (s,3H), 3.07 (dd,1H), 3.08 (dq,1H), 3.76 (s,3H), 3.80 (ddd,1H), 4.98 (dq,1H), 6.1(d,1H)

the 3,4-trans, 4,5-cis, 5,6-cis (tcc) isomer, 0.2 g, m.p. 215°–6° C., n.m.r. (CDCl$_3$): 1.36 (d,3H), 1.41 (d,3H), 2.00 (s,3H), 2.97 (dq,1H), 3.22 (dd,1H), 3.75 (s,3H), 4.19 (ddd,1H), 4.62 (dq,1H), 6.4 (d,1H).

The structures of the ttt and ttc isomers were confirmed by X-Ray analysis.

EXAMPLE 28

To a stirred solution of the product of Example 16 (trans isomer)(1.0 g) in tetrahydrofuran (15 ml) was added 1.0 ml distilled water and 0.2 ml 1N HCl. The solution was stirred at 20°–25° C. for 16 hours. The solvents were evaporated at reduced pressure to give an oil (1.0 g), which was dissolved in trifluoroacetic acid (4.0 ml) at 20°–25° C., then triethylsilane (2.0 ml) was added and the mixture stirred for 16 hours at ambient temperature. The solvents were evaporated to give a gum (1.0 g) which was a mixture of isomers-chromatography on Merck silica eluting with Et$_2$O/hexane gave 2-oxo-3,6-dimethyl-4-benzyloxycarbonylamino-5-benzyloxycarbonyl-3,4,5,6-tetrahydro-2H-pyran (ttt isomer) (200 g) m.p. 110°–2° C. n.m.r.(CDCl$_3$) 1.31 (d,3H), 1.36 (d,3H), 2.65 (dq,1H), 2.85 (dd,1H), 3.95 (ddd,1H), 4.51 (dq,1H), 4.97 (d,1H), 5.04 (s,2H), 5.07 (s,2H), 7.32 (m,10H).

EXAMPLE 29

Ethyl 2-methyl-3-acetylamino-4-(4'-chlorophenylcarbamoyl)-5-oxohexanoate (Example 25) (12 g) was dissolved in trifluoroacetic acid (50 ml), treated with triethylsilane (7.5 ml) and stirred at room temperature for 40 hours. The reaction mixture was diluted with diethyl ether and filtered. The solid was warmed with ethyl acetate then cooled and filtered to give 2-oxo-3,6-dimethyl-4-acetylamino-5-(4'-chlorophenylcarbamoyl)-3,4,5,6-tetrahydro-2H-pyran (ttt isomer) (6.8 g) m.p. 280° C. decomp.

EXAMPLE 30

By the above method was prepared 2-oxo-3,6-dimethyl-4-acetylamino-5[(S)-1'-phenylethylcarbamoyl]-3,4,5,6-tetrahydro-2H-pyran, m.p. 327° C. (decomp.)

(ttt isomer) using the compound of Example 26 as starting material.

EXAMPLE 31

To a solution of methyl 4-acetylamino-2,2-dimethoxy-6-methyl-3,4-dihydro-2H-pyran-5-carboxylate (13.7 g) (Example 23) in methanol (100 ml) at 20°-25° C. was added water (4.0 ml) and 1N HCl (0.4 ml). The mixture was stirred at 20°-25° C. for five hours, then the solvents were evaporated at reduced pressure and the residual gum (13 g) was redissolved in trifluoroacetic acid (100 ml), to which was added methylene chloride (25 ml) and triethylsilane (25 ml). The mixture was stirred at 20°-25° C. for 70 hours and then the solvents were evaporated at reduced pressure. The residue was purified by chromatography on K60 silica eluting with ethyl acetate to give methyl 2-oxo-4-acetylamino-6-methyl-3,4,5,6-tetrahydro-2H-pyran-5-carboxylate (4.0 g) m.p. 135°-6° C. (EtOAc/hexane) (4,5-trans: 5,6-trans isomer).

n.m.r.(CDCl$_3$) 1.41 (d,3H), 1.98 (s,3H), 2.59 (dd,1H), 2.66 (dd,1H), 2.99 (dd,1H), 3.77 (s,3H), 4.53 (m,1H), 4.67 (m,1H), 6.70 (d,1H).

EXAMPLE 32

The mixture of isomers from Example 9 was treated as described in Example 24. Ethyl 2-methyl-3-benzyloxycarbonylamino-4-methoxycarbonyl-5-oxohexanoate (m.p. 51°-3° C.) was purified by chromatography and treated as in Example 27 to yield 2-oxo-3,6-dimethyl-4-benzyloxy-carbonylamino-5-methoxycarbonyl-3,4,5,6-tetrahydro-2H-pyran (ttt isomer) m.p. 144°-6° C., which was purified by chromatography on K60 silica.

REFERENCE EXAMPLES

The following Reference Examples illustrate the means by which compounds of formula I as prepared in Examples 27–32 may be converted into compounds of formula VI which may in turn be converted into compounds of formula VII.

REFERENCE EXAMPLE 1

(a) The product of Example 27 (ttt isomer) (3.0 g) was heated in 10 ml 6N HCl at 95°-100° C. for 16 hours. The solution was allowed to stand at 20° C. for 24 hours, and the crystals were filtered off and dried, giving 2-oxo-3,6-dimethyl-4-amino-3,4,5,6-tetrahydro-2H-pyran-5-carboxylic acid hydrochloride 0.9 g., m.p. 220° C. (decomp), the 3,4-trans, 4,5-trans, 5,6-trans isomer, n.m.r.(d$_6$-DMSO): 1.35 (d,3H), 1.39(d,3H), 2.88 (dd,1H), 2.93 (dq, 1H), 3.66 (dd,1H), 4.56 (dq,1H), 8.7 (broad, 3H).

(b) The product of (a) above (0.30 g) was refluxed in absolute ethanol (10 ml) for 3 hours, then cooled to 20° C. Triethylamine (0.20 ml) and dicyclohexylcarbodiimide (0.30 g) were added to the stirred solution, from which a white powder precipitated after 16 hours. The mixture was filtered, the filtrates evaporated at reduced pressure and the residue flash chromatographed on K60 silica (EtOAc) to give 3-(1-hydroxyethyl)-4-(1-ethoxycarbonylethyl)-trans-azetidin-2-one, having the relative stereochemistry shown in formula VIIa (0.25 g.). n.m.r.(CDCl$_3$): 1.27 (d,3H), 1.30 (t,3H), 1.32 (d,3H), 2.66 (dq,1H), 2.99 (dd,1H), 3.78(dd,1H), 4.18 (q,2H), 4.20 (dq,1H), 6.2 (broad,1H).

REFERENCE EXAMPLE 2

The product of Example 29 (4 g) was dissolved in concentrated hydrochloric acid (20 ml) and heated at 100° C. for 16 hours. The reaction mixture was evaporated, redissolved in concentrated hydrochloric acid (20 ml) and heated at 100° C. for 24 hours. The mixture was evaporated and the residue was washed with ethyl acetate and triturated with ethanol to give 2-oxo-3,6-dimethyl-4-amino-3,4,5,6-tetrahydro-2H-pyran-5-carboxylic acid hydrochloride (ttt isomer), 0.6 g, m.p. 219° C. with decomposition, which can be further treated by the method of Reference Example 1(b) or by other known methods if desired to yield the corresponding azetidone intermediate.

REFERENCE EXAMPLE 3

A solution of the product of Example 31 (1.0 g) in concentrated hydrochloric acid (2.0 ml) was heated at 90°-100° C. for 6 hours. The solution was evaporated at reduced pressure and the residual foam triturated with boiling acetonitrile (10 ml) to give, after filtration, 2-oxo-4-amino-6-methyl-3,4,5,6-tetrahydro-2H-pyran-5-carboxylic acid hydrochloride (0.65 g) m.p. 195°-decomp. (trans, trans isomer)

n.m.r.(d$_6$-DMSO): 1.35 (d,3H), 2.70 (dd,1H), 2.75 (dd,1H), 3.18 (dd,1H), 4.00 (m,1H), 4.52 (m,1H), 8.7 (broad, 3H).

The product can be further treated according to the method of Reference Example 1 (b) or by other known methods to yield the corresponding azetidinone intermediate.

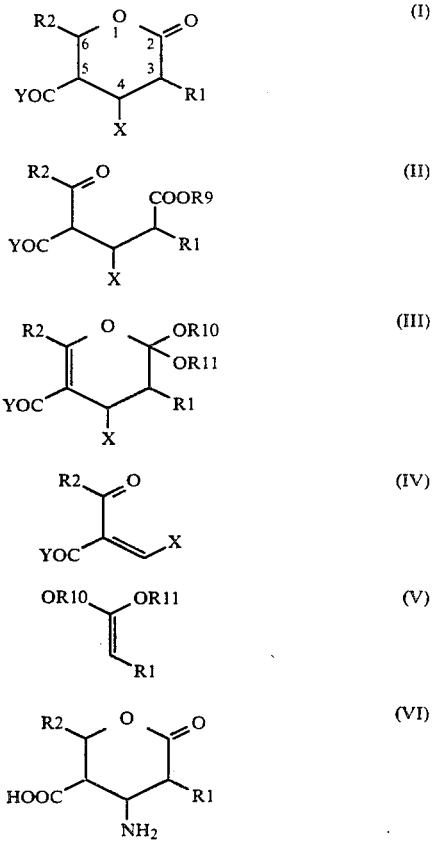

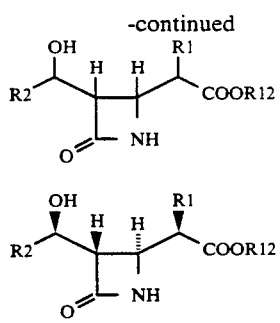

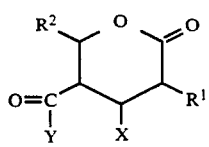

We claim:
1. A tetrahydropyran derivative of the formula (I):

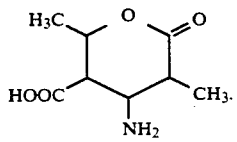

wherein:
R$^1$ is alkyl;
R$^2$ is alkyl or substituted alkyl;
X is a group —NHCVR$^4$ wherein V is oxygen or sulphur, and R$^4$ is hydrogen, alkyl, substituted alkyl, cycloalkyl, alkenyl, aryl, arylalkyl, amino-, mono- or di-alkylamino, or R$^4$ is —OR$^5$ wherein R$^5$ is alkyl, substituted alkyl, aryl, arylalkyl;
Y is alkoxy, substituted alkoxy, cycloalkoxy, substituted cycloalkoxy, arylalkoxy;
or X can be amino, in which case, Y is a group —OH;
wherein alkyl means C$_{1-6}$ alkyl; substituted alkyl means alkyl substituted by at least one alkoxy group or halogen atom; cycloalkyl means C$_{3-7}$ cycloalkyl or bridged C$_{6-9}$ bicycloalkyl; alkenyl means C$_{2-6}$ alkenyl; aryl means phenyl, phenyl substituted by halogen, alkyl, alkoxy or alkoxycarbonyl; substituted alkoxy means alkoxy substituted by carboxy or C$_{1-4}$alkoxycarbonyl; and substituted cycloalkoxy means cycloalkoxy substituted by carboxy or C$_{1-4}$alkoxycarbonyl.

2. A tetrahydropyran derivative as claimed in claim 1 wherein:
R1 is 1-4C alkyl;
R2 is alkyl or alkyl substituted by at least one 1-4C alkoxy group or halogen atom;
arylalkyl; or X is a group —NHCVR$^4$ wherein V is oxygen, R$^4$ is hydrogen, alkyl, substituted alkyl, cycloalkyl, substituted cycloalkyl, alkenyl, aryl, arylalkyl, amino, mono- or di 1-4 C alkylamino or R$^4$ is —OR$^5$ wherein R$^5$ is alkyl, substituted alkyl, aryl or arylalkyl;
Y is alkoxy, substituted alkoxy, cycloalkoxy, arylalkoxy.

3. A tetrahydropyran derivative as claimed in claim 1 wherein R$^1$ represents a methyl group.

4. A tetrahydropyran derivative as claimed in claim 1 wherein R$^2$ represents a methyl group or a methyl group substituted by at least one fluorine atom.

5. A tetrahydropyran derivative as claimed in claim 1 wherein X represents —NHCOR$^4$ wherein R$^4$ represents hydrogen, methyl, ethyl, ethenyl, phenyl, benzyl, methoxy, ethoxy, amino, trifluoroethoxy, trichloroethoxy, phenoxy or benzyloxy.

6. A tetrahydropyran derivative as claimed in claim 1 wherein Y represents methoxy, ethoxy, benzyloxy.

7. An optically active tetrahydropyran derivative of the following formula

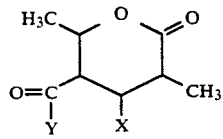

8. An optically active tetrahydropyran derivative of the formula

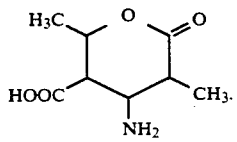

wherein
X is a group of the formula —NHCVR$^4$ wherein V is oxygen and R$^4$ is methoxy or ethoxy; and
Y is methoxy, ethoxy or benzyloxy.

9. The tetrahydropyran derivative according to claim 1 wherein said derivative is optically active.

* * * * *